US005728656A

United States Patent [19]
Yamaguchi et al.

[11] Patent Number: 5,728,656
[45] Date of Patent: Mar. 17, 1998

[54] LOWER-ASH LUBRICATING OIL HAVING ULTRA-NEUTRAL ZINC DIALKYLDITHIOPHOSPHATES

[75] Inventors: Elaine S. Yamaguchi, El Cerrito; William R. Ruhe, Jr., Benecia, both of Calif.

[73] Assignee: Chevron Chemical Company, San Ramon, Calif.

[21] Appl. No.: 822,251

[22] Filed: Mar. 20, 1997

[51] Int. Cl.$^6$ ................................................ C10M 137/10
[52] U.S. Cl. ................................................ 508/371
[58] Field of Search ................................................ 508/371

[56] References Cited

U.S. PATENT DOCUMENTS

| | | | |
|---|---|---|---|
| 3,691,220 | 9/1972 | Horodysky | 260/429.9 |
| 4,094,800 | 6/1978 | Warne | 252/32.7 E |
| 4,101,428 | 7/1978 | Crawford | 508/371 |
| 4,592,851 | 6/1986 | Stadtmiller et al. | 252/32.7 E |
| 5,326,485 | 7/1994 | Cervenka et al. | 508/371 |
| 5,380,448 | 1/1995 | Kadkhodayan et al. | 252/32.7 E |
| 5,384,054 | 1/1995 | Kadkhodayan | 252/32.7 E |
| 5,604,188 | 2/1997 | Ryan | 508/371 |

*Primary Examiner*—Jacqueline V. Howard
*Attorney, Agent, or Firm*—Ernest A. Schaal

[57] ABSTRACT

A lubricating oil composition, having an ash content of less than 1.5 weight percent, has a base oil of lubricating viscosity, and a zinc dialkyldithiophosphate having a zinc to phosphorus weight ratio in the range of from 0.95:1 to 1.04:1.

12 Claims, No Drawings

LOWER-ASH LUBRICATING OIL HAVING ULTRA-NEUTRAL ZINC DIALKYLDITHIOPHOSPHATES

The present invention relates to a lower-ash lubricating oil having ultra-neutral zinc dialkyldithiophosphates as antiwear agents.

BACKGROUND OF THE INVENTION

It is well known that various additives can be used in lubricating oils in order to improve certain oil properties and to make a more satisfactory lubricant. For example, antiwear agents decrease wear of machine parts. Wear inhibitors are incorporated in motor oils and industrial oils to prevent wear of moving parts in high performance engines. Numerous other additives have been developed for use in such oil compositions to improve the lubricating characteristics thereof and to lessen the wear of the moving parts.

Of the antiwear agents, zinc dialkyldithiophosphates (ZnDTP) have long been used as antiwear additives and antioxidants in hydraulic oils, motor oils, automatic transmission fluids, and the like. Processes for the production of zinc dialkyldithiophosphates are well known. See U.S. Pat. Nos. 2,838,555; 3,848,032; 4,085,053; 4,123,370; 4,215,067; and 4,263,150, which are all hereby incorporated by reference for all purposes. In a typical reaction, four equivalents of a hydroxy alkyl compound are reacted with phosphorus pentasulfide. Once formed, the dialkyldithiophosphoric acid is then neutralized with an excess of zinc oxide.

An important characteristic in determining the antiwear properties of the zinc dialkyldithiophosphate is the zinc to phosphorus ratio. Typically, the conventional wisdom was that the zinc to phosphorus ratio should be no less than about 1.15:1, and preferably greater than about 1.20:1.

U.S. Pat. No. 3,691,220

This patent teaches a process for preparing an overbased zinc dithiophosphate. It states that "neutral" zinc dithiophosphate have a zinc to phosphorus ratio of 1.06:1.

U.S. Pat. No. 4,094,800

This patent teaches a lubricating oil composition that has a base oil, either an alcohol or amine, and a primary zinc dialkyldithiophosphate that has a zinc to phosphorus weight ratio of 1.15:1 to 1.5:1, and a preferred zinc to phosphorus weight ratio of 1.15:1 to 1.35:1.

U.S. Pat. No. 4,592,851

This patent teaches a lubricating oil composition that has a base oil and a primary zinc dialkyldithiophosphate that has a zinc to phosphorus weight ratio of 1.15:1 to 1.65:1, and a preferred zinc to phosphorus weight ratio of 1.20:1 to 1.5:1.

U.S. Pat. No. 5,326,485

This patent teaches a low ash lubricating oil composition that has an antioxidant, an overbased alkaline earth metal sulfurized alkyl phenate, and a primary zinc dialkyldithiophosphate. The basic to neutral salt ratio of the zinc dialkyldithiophosphate is at least 0.96 by $^{31}P$ nuclear magnetic resonance (NMR) spectroscopy.

U.S. Pat. No. 5,380,448

This patent teaches a process for making an overbased zinc salt of dialkyldithiophosphate that has a zinc to phosphorus weight ratio of 1.2:1 to 1.3:1.

U.S. Pat. No. 5,384,054

This patent teaches a process for making an overbased zinc salt of dialkyldithiophosphate that has a zinc to phosphorus weight ratio of 1.15:1 to 1.3:1.

SUMMARY OF THE INVENTION

The present invention provides a lower-ash lubricating oil composition having superior antiwear performance. That lower-ash lubricating oil composition has a base oil of lubricating viscosity and an ultra-neutral zinc dialkyldithiophosphate.

The present invention comes out of basic research in the field of zinc dialkyldithiophosphates. We have discovered that ultra-neutral zinc salts of dialkyldithiophosphates give better antiwear performance than basic zinc salts of dialkyldithiophosphates. This is surprising because conventional wisdom has always been that basic zinc dialkyldithiophosphate salts give better performance.

We are unsure as to the mechanism that causes this improvement, but we think that the ultra-neutral zinc dialkyldithiophosphate salts tend to exist as oligomers in solution, while the basic salts tend to exist as a single entity. In solution, the ultra-neutral salts would have a greater tendency to adsorb onto the surface because there are more polar functional groups per unit. Without the adsorption step, wear inhibition cannot take place. Larger oligomers tend to adsorb preferentially to the metal surface, thus providing anti-wear. As these larger oligomers are adsorbed, the equilibrium in solution is shifted toward re-equilibrating to provide more of these larger oligomers. Basic salts do not interact with the metal surface as favorably. This phenomenon was not seen in previous work because most anti-wear bench tests do not show the effects of adsorption.

By "ultra-neutral zinc dialkyldithiophosphate," we mean a zinc dialkyldithiophosphate having a zinc to phosphorus weight ratio in the range of from 0.95:1 to 1.04:1. Ultra-neutral zinc dialkyldithiophosphates are distinguished from "neutral" zinc dialkyldithiophosphates in that they have a lower zinc to phosphorus ratio. Conventional wisdom has always been that "neutral" zinc dialkyldithiophosphates have a zinc to phosphorus ratio of 1.05:1 or 1.06:1.

Conventional $^{31}P$ NMR procedures were used to assay the amount of neutral or basic zinc dialkyldithiophosphate. In accordance with these procedures, the basic species from a primary zinc dialkyldithiophosphate appears in the range of about 103 to 105 ppm in the spectrum, whereas that derived from a secondary zinc dialkyldithiophosphate appears in the range of about 98 to 100 ppm in the spectrum. On the other hand, the neutral species from a primary zinc dialkyldithiophosphate appears in the range of about 100 to 102 ppm in the spectrum, whereas that derived from a secondary zinc dialkyldithiophosphate appears in the range of about 92 to 94 ppm. The signals are integrated in the usual manner to calculate the relative amounts.

Prior references teach that a neutral zinc dialkyldithiophosphate salt has a zinc to phosphorus weight ratio of 1.05:1 because it was assumed that zinc dialkyldithiophosphates had the following structure (R and R' being alkyl groups).

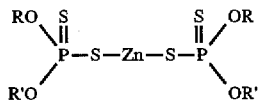

We have found that zinc dialkyldithiophosphate salts having a zinc to phosphorus weight ratio of 1.05 contain approximately 10 weight percent basic salts, as determined by $^{31}P$ NMR spectroscopy. We have also found that zinc dialkyldithiophosphate salts having lower zinc to phosphorus weight ratios give better antiwear properties without being deleterious to other properties.

The ash content of lubricating oils varies considerably, but for the purposes of this application, the term "lower-ash" means an ash content of less than 1.5 weight percent. Preferably, the ash content of the lubricating oil composition is less than 1.1 weight percent, more preferably less than 1.0 weight percent. The ash content of the lubricating oil composition should be low in order to prevent deterioration of the anti-wear properties of the zinc dialkyldithiophosphate.

Preferably, each of the alkyl groups of the zinc dialkyldithiophosphate contains from 3 to 20 carbon atoms. More preferably, each of the alkyl groups contains from 3 to 8 carbon atoms. Preferably, each of the alkyl groups of the zinc dialkyldithiophosphate is a secondary alkyl group.

In one embodiment, the low ash lubricating oil composition has a base oil of lubricating viscosity, an ashless dispersant, an overbased sulfurized alkylphenate detergent, an oxidation inhibitor, a viscosity index improver, and the ultra-neutral zinc dialkyldithiophosphate.

DETAILED DESCRIPTION OF THE INVENTION

In its broadest aspect, the present invention involves a lower-ash lubricating oil composition having superior antiwear performance. That lower-ash lubricating oil composition has a base oil of lubricating viscosity and an ultra-neutral zinc dialkyldithiophosphate. The ultra-neutral zinc dialkyldithiophosphate is generally incorporated into an engine oil in an amount of 0.05 to 5 weight percent, preferably 0.05 to 3 weight percent, per total amount of the engine oil.

The ultra-neutral zinc dialkyldithiophosphate can be produced from a dialkyldithiophosphoric acid of the formula:

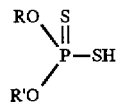

The hydroxy alkyl compounds from which the dialkyldithiophosphoric acids are derived can be represented generically by the formula ROH or R'OH, where R or R' is alkyl or substituted alkyl group. Preferably, R or R' is a branched, non-branched, or cyclic alkyl containing 3 to 20 carbon atoms; more preferably, a branched, non-branched, or cyclic secondary alkyl containing 3 to 8 carbon atoms; most preferably, a dialkyldithiophosphoric acid wherein the alkyl group is derived from a secondary alcohol blend containing an average of about 4.5 carbons per molecule.

Mixtures of hydroxy alkyl compounds may also be used. As is recognized in the art, these hydroxy alkyl compounds need not be monohydroxy alkyl compounds. That is, the dialkyldithiophosphoric acids may be prepared from mono-, di-, tri-, tetra-, and other polyhydroxy alkyl compounds, or mixtures of two or more of the foregoing. It is to be understood that most commercially available alcohols are not pure compounds but are mixtures containing a predominant amount of the desired alcohol and minor amounts of various isomers and/or longer or shorter chain alcohols.

Examples of the general class of compounds corresponding to the formula ROH or R'OH are those wherein R or R' are selected from an alkyl, cycloalkyl, alkyl-substituted cycloalkyl, alkoxyalkyl, haloalkyl, and the like. Specific examples of such hydroxy alkyl compounds are 4-methyl-2-pentanol, 2-butanol, octyl alcohol, cyclohexanol, 2-ethylhexanol, isopropanol, methylcyclohexanol, cyclohexanol, cyclopentanol, butanol, isoamyl alcohol, oleyl alcohol, dodecanol, lauryl alcohol, cetyl alcohol, ethylene glycol, propylene glycol, octylphenoxyethanol, neopentyl alcohol, isohexyl alcohol, 2,3-dimethylbutanol, n-heptanol, diisopropyl carbinol, glycerol, diethylene glycol, capryl alcohol, and the like.

The phosphorus pentasulfide reactant used in the dialkyldithiophosphoric acid formation step of this invention may contain minor amounts of any one or more of $P_2S_3$, $P_4S_3$, $P_4S_7$, or $P_4S_9$. Such phosphorus sulfide compositions may contain minor amounts of free sulfur.

While the structure of phosphorus pentasulfide is generally represented as $P_2S_5$, the actual structure is believed to contain four phosphorus atoms and ten sulfur atoms, i.e., $P_4S_{10}$. For the purposes of this invention, the phosphorus sulfide reactant will be considered as a compound having the structure of $P_2S_5$ with the understanding that the actual structure is probably $P_4S_{10}$.

LUBRICATING OIL COMPOSITIONS

The ultra-neutral zinc dialkyldithiophosphates of this invention are useful as lubricating oil additives imparting antiwear properties to the lubricating oil. Such lubricating oil compositions are useful in diesel engines, gasoline engines, as well as in marine engines.

Such lubricating oil compositions employ a finished lubricating oil, which may be single or multigrade. Multigrade lubricating oils are prepared by adding viscosity index (VI) improvers.

The lubricating oil, or base oil, used in such compositions may be mineral oil or synthetic oils of viscosity suitable for use in the crankcase of an internal combustion engine, such as gasoline engines and diesel engines, which include marine engines. Crankcase lubricating oils ordinarily have a viscosity of about 1300 cSt at 0° F. to 24 cSt at 210° F. (99° C.). The lubricating oils may be derived from synthetic or natural sources. Mineral oil for use as the base oil in this invention includes paraffinic, naphthenic, and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins, such as 1-decene trimer. Likewise, alkyl benzenes of proper viscosity, such as didodecyl benzene, can be used. Useful synthetic esters include the esters of both monocarboxylic acid and polycarboxylic acids, as well as monohydroxy alkanols and polyols. Typical examples are didodecyl adipate, pentaerythritol tetracaproate, di-2-ethylhexyl adipate, dilaurylsebacate, and the like. Complex esters prepared from mixtures of mono and dicarboxylic acids and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

The lubricating oil composition may also contain small amounts of ashless dispersants, phenate and sulfonate detergents, rust inhibitors, foam inhibitors, corrosion inhibitors, metal deactivators, pour point depressants, antioxidants, and a variety of other well-known additives.

ASHLESS DISPERSANT

Examples of the ashless dispersants useful in the present invention include succinimides and succinic esters, each of which has an alkyl or alkenyl group of a molecular weight of about 700 to 3,000. In addition to these compounds, their derivatives (e.g., borated derivatives) are also employable. The ashless dispersant is generally incorporated into an engine oil in an amount of 0 to 20 weight percent, preferably 1 to 10 weight percent, per total amount of the engine oil.

OVERBASED SULFURIZED ALKYLPHENATE

Examples of overbased sulfurized alkylphenates useful in the present invention include those described, for example, in U.S. Pat. Nos. 2,680,096; 3,178,368; 3,367,867; 3,801,507; 5,529,705; and the like, which are all hereby incorporated by reference for all purposes. The overbased sulfurized alkylphenate is generally incorporated into an engine oil in an amount of 0 to 20 weight percent, preferably 1 to 10 weight percent, per total amount of the engine oil.

OXIDATION INHIBITORS

Examples of oxidation inhibitors useful in the present invention include, but are not limited to, phenol type (phenolic) oxidation inhibitors, such as 4,4'-methylene-bis (2,6-di-tert-butylphenol), 4,4'-bis(2,6-di-tert-butylphenol), 4,4'-bis(2-methyl-6-tert-butylphenol), 2,2'-methylene-bis(4-methyl-6-tert-butyl-phenol), 4,4'-butylidene-bis(3-methyl-6-tert-butylphenol), 4,4'-isopropylidene-bis(2,6-di-tert-butylphenol), 2,2'-methylene-bis(4-methyl-6-nonylphenol), 2,2'-isobutylidene-bis(4,6-dimethylphenol), 2,2'-methylene-bis(4-methyl-6-cyclohexylphenol), 2,6-di-tert-butyl-4-methylphenol, 2,6-di-tert-butyl-4-ethylphenol, 2,4-dimethyl-6-tert-butyl-phenol, 2,6-di-tert-α-dimethylamino-p-cresol, 2,6-di-tert-4-(N,N'-dimethylaminomethylphenol), 4,4'-thiobis(2-methyl-6-tert-butylphenol), 2,2'-thiobis(4-methyl-6-tert-butylphenol), bis(3-methyl-4-hydroxy-5-tert-butylbenzyl)-sulfide, and bis(3,5-di-tert-butyl-4-hydroxybenzyl). Diphenylamine-type oxidation inhibitors include, but are not limited to, alkylated diphenylamine, phenyl-α-naphthylamine, and alkylated α-naphthylamine. Other types of oxidiation inhibitors include metal dithiocarbamate (e.g., zinc dithiocarbamate), and methylenebis (dibutyldithiocarbamate). The oxidation inhibitor is generally incorporated into an engine oil in an amount of 0 to 10 weight percent, preferably 0.05 to 2 weight percent, per total amount of the engine oil.

VISCOSITY INDEX IMPROVER

Examples of viscosity index improvers useful in the present invention include poly-(alkyl methacrylate), ethylene-propylene copolymer, styrene-butadiene copolymer, and polyisoprene. Viscosity index improvers of dispersant type (having increased dispersancy) or multifunction type are also employed. These viscosity index improvers can be used singly or in combination. The viscosity index improver is generally incorporated into an engine oil in an amount of 0 to 20 weight percent, preferably 1 to 15 weight percent, per total amount of the engine oil.

A lubricating oil composition can be produced by blending together a major amount of a base oil of lubricating viscosity, from 0 to 20 weight % of an ashless dispersant, from 0 to 20 weight % of an overbased sulfurized alkylphenate detergent, from 0 to 10 weight % of an oxidation inhibitor, from 0 to 20 weight % of a viscosity index improver; and, from 0.05 to 5 weight % of a zinc dialkyldithiophosphate, wherein said zinc dialkyldithiophosphate has a zinc to phosphorus weight ratio in the range of from 0.95:1 to 1.04:1, wherein the ash content of said lubricating oil composition is less than 1.5 weight percent. The lubricating oil composition produced by that method might have a slightly different composition, as components interact.

EXAMPLES

The invention will be further illustrated by the following examples, which set forth particularly advantageous method embodiments. While the Examples are provided to illustrate the present invention, they are not intended to limit it.

Example 1

Preparation of an Ultra-Neutral Zinc Dialkyldithiophosphate Salt

An ultra-neutral zinc dialkyldithiophosphate salt was prepared by the following process, from a dialkyldithiophosphoric acid wherein the alkyl group was derived from a secondary alcohol blend containing an average of about 4.5 carbons per molecule. 1164 grams of 100 neutral oil, 8.7 grams of acetic acid, and about two-thirds (2034 grams) of the total dialkyldithiophosphoric acid charge were charged into a stirred round bottom glass flask. 437 grams of zinc oxide was then charged to the reaction mixture. The remaining dialkyldithiophosphoric acid (1017 grams) was added at a rate such that the temperature of the mixture did not exceed 77° C. Once all the dialkyldithiophosphoric acid was added, the temperature of the reaction mixture was held at approximately 77° C. for three hours. After throe hours, the reaction mixture was heated to 99° C., and vacuum was applied for thirty minutes to strip off any water and/or unreacted alcohol. The product was filtered using diatomaceous earth filter aid. The zinc and phosphorus content of this material were measured, and the zinc to phosphorus ratio was calculated to be 0.98. No basic salt was detected by $^{31}$P NMR.

Example 2

Comparison of Basic and Ultra-Neutral Zinc Dialkyldithiophosphate Salts

Basic and ultra-neutral zinc dialkyldithiophosphate salts were synthesized using a different procedure than that shown in Example 1. Each salt was blended into a oil formulation containing: Group I base stock, 8 weight percent of an ashless dispersant, 53 mmoles/kg of a metallic detergent, 0.2 weight percent of an oxidation inhibitor, and a non-dispersant olefin copolymer viscosity index improver to achieve SAE15W-40 grade lubricating oils. These oils were tested in the ASTM Sequence VE engine test, which utilizes a Ford 2.3 liter four-cylinder engine. The test method simulates a type of severe field test service characterized by a combination of low speed, low temperature "stop and go" city driving and moderate turnpike operation. The effectiveness of the additives in the oil is measured in terms of the protection provided against valve train wear. The Sequence VE wear results are shown in Table I.

TABLE I

Ultra-Neutral ZnDTP versus Basic ZnDTP Wear Performance in Sequence VE Engine Test.

| | Zn:P Ratio | Average Cam Wear | Maximum Cam Wear |
|---|---|---|---|
| Basic Salt ZnDTP | 1.27:1 | 7.62 ± 4.02 | 17.2 ± 3.75 |
| Ultra-Neutral Salt ZnDTP | 0.98:1 | 0.80 ± 0.94 | 3.83 ± 5.86 |

The data show that the ultra-neutral zinc dialkyldithiophosphate salt provided better wear performance than the basic zinc dialkyldithiophosphate salt under these test conditions, as measured by average cam wear and maximum cam wear. Tables II and III show the statistical analyses of the engine test data. Theies analyses show that there is a high confidence level in this wear data.

TABLE II

Statistical Analysis of Sequence VE Wear Performance
(Square Root of Average Cam Wear (ACW))

| Zinc Type | n | Mean | p-Value (Conclusion) |
|---|---|---|---|
| Basic Salt ZnDTP | 3 | 2.68 | 0.027 (Significant Difference) |
| Ultra-Neutral Salt ZnDTP | 3 | 0.80 | |

ZnDTP Type: There is a statistically significant difference between zinc dialkyldithiophosphate types for average square root of ACW (p=0.027, 97.3 percent confidence level).

TABLE III

Statistical Analysis of Sequence VE Wear Performance
(Square Root of Maximum Cam Wear (MCW))

| Zinc Type | n | Mean | p-Value (Conclusion) |
|---|---|---|---|
| Basic Salt ZnDTP | 3 | 4.13 | 0.045 (Significant Difference) |
| Ultra-Neutral Salt ZnDTP | 3 | 1.53 | |

ZnDTP Type: There is a statistically significant difference between zinc dialkyldithiophosphate types for average square root of MCW (p=0.045, 95.5 percent confidence level).

Example 3

Ultra-Neutral Zinc Dialkyldithiophosphate Salt Corrosion Test Results

An ultra-neutral zinc dialkyldithiophosphate salt was prepared from a dialkyldithiophosphoric acid wherein the alkyl group is derived from a secondary alcohol blend containing an average of about 4.5 carbons per molecule. The derived ultra-neutral zinc dialkyldithiophosphate had a Zn:P ratio of 0.98:1, which was less than the theoretical 1.05:1 of neutral zinc dialkyldithiophosphate and found to have a low corrosivity to carbon steel.

The corrosion test was run as follows: Three new carbon steel (Type 1018) test coupons, approximately 2×2 inches square, were individually weighed to four decimal places. The coupons were suspended by teflon tape in a glass vessel containing sufficient secondary zinc dialkyldithiophosphate to totally immerse the coupons. The secondary zinc dialkyldithiophosphate had a zinc to phosphorus ratio of 0.98:1 and contained no basic salt according to $^{31}$P NMR analysis. The vessel containing the coupons and the zinc dialkyldithiophosphate was placed into a 52° C. oven. The first coupon was removed from the test liquid after 72 hours for inspection. It was gently cleaned with cleanser to remove any scale that had formed. It was then rinsed with water and sonicated in methanol for five minutes. The cleaned coupon was then dried in a 100° F. oven. The coupon was weighed, and the corrosion rate was calculated to be 0.62 mils/year based on its weight loss and exposure time. A second coupon was removed after 198 hours. It was cleaned using the previously mentioned procedure. The corrosion rate measured for this coupon was 0.27 mils/year. The third coupon was removed after 720 hours, and it was cleaned using the cleaning procedure mentioned previously. The corrosion rate measured for this coupon was 0.05 mils/year. The test results are shown in Table IV.

TABLE IV

Ultra-Neutral Salt/Carbon Steel Corrosion Test Results.

| | | Corrosion Rate | | |
|---|---|---|---|---|
| % Basic Salt | Exposure Temp. | mils per year after | | |
| Zn:P | by NMR | (°C.) | 72 hr. | 198 hr. | 720 hr. |
| 0.98 | 0.0 | 52 | 0.62 | 0.27 | 0.05 |

Example 4

Crude Sediment for Ultra-Neutral Zinc Dialkyldithiophosphate Salt

Zinc dialkyldithiophosphate with less that 1.05:1 Zn:P ratio tend to produce less sediment during the manufacturing process than zinc dialkyldithiophosphate made with higher Zn:P ratios.

An ultra-neutral secondary zinc dialkyldithiophosphate salt was prepared by charging 124.9 grams of 100 neutral oil, 1.0 gram of acetic acid and about two-thirds (218.3 grams) of the total dialkyldithiophosphoric acid charge into a stirred round bottom glass flask. 48.4 grams of zinc oxide was then charged to the reaction mixture. The remaining dialkyldithiophosphoric acid (109.2 grams) was added at a rate such that the temperature of the mixture did not exceed 77° C. Once all the dialkyldithiophosphoric acid was added, the temperature of the reaction mixture was held at approximately 77° C. for three hours. After three hours, the reaction mixture was heated to approximately 97° C., and vacuum was applied for 30 minutes to strip off any water and/or unreacted alcohol. The product was diluted with hexane and centrifuged to separate any sediment. The hexane solution was decanted from the sediment and discarded. The sediment was washed with hexane, re-centrifuged, and the liquid was decanted. This washing procedure was repeated. The sediment was dried and weighed. The sediment was determined to be 0.05 weight percent. The zinc and phosphorus content of this material was measured, and the zinc to phosphorus ratio was calculated to be 1.01:1 and no basic salt was detected by $^{31}$P NMR.

Comparative Example 4A

Crude Sediment for Neutral Zinc Dialkyldithiophosphate Salt

Using the same dialkyldithiophosphoric acid as used in Example 4, another preparation of secondary zinc dialkyldithiophosphate salt was made by charging 128.2 grams of 100 neutral oil, 1.0 gram of acetic acid and about two-thirds (224.1 grams) of the total dialkyldithiophosphoric acid charge into a stirred round bottom glass flask. 51.7 grams of zinc oxide was then charged to the reaction mixture. The remaining dialkyldithiophosphoric acid (112.1 grams) was added at a rate such that the temperature of the mixture did not exceed 77° C. Once all the dialkyldithiophosphoric acid was added, the temperature of the reaction mixture was held at approximately 77° C. for three hours. After three hours, the reaction mixture was heated to approximately 97° C., and vacuum was applied for 30 minutes to strip off any water and/or unreacted alcohol. The product was diluted with hexane and centrifuged to separate any sediment. The hexane solution was decanted from the sediment. The sediment was washed with hexane, re-centrifuged, and the liquid was decanted. This washing procedure was repeated. The sediment was determined to be 0.04 weight percent. The zinc and phosphorus content of this material was measured, and the zinc to phosphorus ratio was calculated to be 1.06. This material contained 14 weight percent basic salt (relative to the total neutral and basic salts) as determined by $^{31}$P NMR.

Comparative Example 4B

Crude Sediment for Basic Zinc Dialkyldithiophosphate Salt

Using the same dialkyldithiophosphoric acid as used in Example 4, another preparation of a secondary zinc dialkyldithiophosphate salt was made by charging 95.1 grams of 100 neutral oil, 0.8 grams of acetic acid and about two-thirds (166.3 grams) of the total dialkyldithiophosphoric acid charge into a stirred round bottom glass flask. 39.9 grams of zinc oxide was then charged to the reaction mixture. The remaining dialkyldithiophosphoric acid (83.1 grams) was added at a rate such that the temperature of the mixture did not exceed 77° C. Once all the dialkyldithiophosphoric acid was added, the temperature of the reaction mixture was held at approximately 77° C. for three hours. After three hours, the reaction mixture was heated to approximately 98° C., and vacuum was applied for 30 minutes to strip off any water and/or unreacted alcohol. The product was diluted with hexane and centrifuged to separate any sediment. The hexane solution was decanted from the sediment. The sediment was washed with hexane, re-centrifuged, and the liquid was decanted. This washing procedure was repeated. The sediment was dried and weighed. The sediment was determined to be 0.09 weight percent. The zinc and phosphorus content of this material was measured, and the zinc to phosphorus ratio was calculated to be 1.09. This material contained 22 weight percent basic salt (relative to the total neutral and basic salts) as determined by $^{31}$P NMR.

Comparative Example 4C

Crude Sediment for Basic Zinc Dialkyldithiophosphate Salt

Using the same dialkyldithiophosphoric acid as used in Example 4, another preparation of a secondary zinc dialkyldithiophosphate salt was made by charging 94.7 grams of 100 neutral oil, 0.8 grams of acetic acid and about two-thirds (165.5 grams) of the total dialkyldithiophosphoric acid charge into a stirred round bottom glass flask. 41.2 grams of zinc oxide was then charged to the reaction mixture. The remaining dialkyldithiophosphoric acid (82.7 grams) was added at a rate such that the temperature of the mixture did not exceed 77° C. Once all the dialkyldithiophosphoric acid was added, the temperature of the reaction mixture was held at approximately 77° C. for three hours. After three hours, the reaction mixture was heated to approximately 99° C., and vacuum was applied for 30 minutes to strip off any water and/or unreacted alcohol. The product was diluted with hexane and centrifuged to separate any sediment. The hexane solution was decanted from the sediment. The sediment was washed with hexane, re-centrifuged, and the liquid was decanted. This washing procedure was repeated. The sediment was dried and weighed. The sediment was determined to be 0.28 weight percent. The zinc and phosphorus content of this material was measured, and the zinc to phosphorus ratio was calculated to be 1.11. This material contained 27 weight percent basic salt (relative to the total neutral and basic salts) as determined by $^{31}$P NMR.

While the present invention has been described with reference to specific embodiments, this application is intended to cover those various changes and substitutions that may be made by those skilled in the art without departing from the spirit and scope of the appended claims.

What is claimed is:

1. A lubricating oil composition comprising:
    (a) a base oil of lubricating viscosity; and
    (b) a zinc dialkyldithiophosphate, wherein said zinc dialkyldithiophosphate has a zinc to phosphorus weight ratio in the range of from 0.95:1 to 1.04:1; and
   wherein the ash content of said lubricating oil composition is less than 1.5 weight percent.

2. A lubricating oil composition according to claim 1 wherein the ash content of said lubricating oil composition is less than 1.1 weight percent.

3. A lubricating oil composition according to claim 2 wherein the ash content of said lubricating oil composition is less than 1.0 weight percent.

4. A lubricating oil composition according to claim 3 wherein each of the alkyl groups of said zinc dialkyldithiophosphate contains from 3 to 20 carbon atoms.

5. A lubricating oil composition according to claim 4 wherein each of the alkyl groups of said zinc dialkyldithiophosphate contains from 3 to 8 carbon atoms.

6. A lubricating oil composition according to claim 4 wherein each of the alkyl groups of said zinc dialkyldithiophosphate is a secondary alkyl group.

7. A lubricating oil composition according to claim 2 further comprising an overbased sulfurized alkylphenate detergent.

8. A lubricating oil composition comprising:
    (a) a major amount of a base oil of lubricating viscosity;
    (b) from 0 to 20 weight % of an ashless dispersant;
    (c) from 0 to 20 weight % of an overbased sulfurized alkylphenate detergent;
    (d) from 0 to 10 weight % of an oxidation inhibitor;
    (e) from 0 to 20 weight % of a viscosity index improver; and
    (f) from 0.05 to 5 weight % of a zinc dialkyldithiophosphate, wherein said zinc dialkyldithiophosphate has a zinc to phosphorus weight ratio in the range of from 0.95:1 to 1.04:1; and
   wherein the ash content of said lubricating oil composition is less than 1.5 weight percent.

9. A lubricating oil composition comprising:
    (a) a major amount of a base oil of lubricating viscosity;
    (b) from 1 to 10 weight % of an ashless dispersant;
    (c) from 1 to 10 weight % of an overbased sulfurized alkylphenate detergent;
    (d) from 0.05 to 2 weight % of an oxidation inhibitor;
    (e) from 1 to 15 weight % of a viscosity index improver; and
    (f) from 0.05 to 3 weight % of a zinc dialkyldithiophosphate, wherein said zinc dialkyldithiophosphate has a zinc to phosphorus weight ratio in the range of from 0.95:1 to 1.04:1; and
   wherein the ash content of said lubricating oil composition is less than 1.5 weight percent.

10. A method of decreasing the wear of machine parts, said method comprising lubricating said parts with the lubricating oil composition according to claim 1.

11. A method of producing a lubricating oil composition comprising blending the following components together:
    (a) a major amount of a base oil of lubricating viscosity;
    (b) from 0 to 20 weight % of an ashless dispersant;

(c) from 0 to 20 weight % of an overbased sulfurized alkylphenate detergent;

(d) from 0 to 10 weight % of an oxidation inhibitor;

(e) from 0 to 20 weight % of a viscosity index improver; and (f) from 0.05 to 5 weight % of a zinc dialkyl dithiophosphate, wherein said zinc dialkyldithiophosphate has a zinc to phosphorus weight ratio in the range of from 0.95:1 to 1.04:1;

wherein the ash content of said lubricating oil composition is less than 1.5 weight percent.

12. A lubricating oil composition produced by the method according to claim 11.

* * * * *